United States Patent [19]

Koenen et al.

[11] Patent Number: 5,283,722

[45] Date of Patent: Feb. 1, 1994

[54] SURGICAL-TYPE GLOVE AND ILLUMINATOR ASSEMBLY

[76] Inventors: Howard P. Koenen; Raymond W. Trow, both of 1526 E. Lind St., Tucson, Ariz. 85719

[21] Appl. No.: 926,164

[22] Filed: Aug. 5, 1992

[51] Int. Cl.$^5$ .............................................. F21L 15/08
[52] U.S. Cl. ........................................ 362/103; 362/32
[58] Field of Search ........................ 362/103, 32, 802

[56] References Cited

U.S. PATENT DOCUMENTS

| | | | |
|---|---|---|---|
| 455,972 | 7/1891 | Oudin et al. | 362/103 |
| 914,975 | 3/1909 | Radley | 362/103 |
| 1,173,269 | 2/1916 | Heidemann | 362/103 |
| 1,553,860 | 9/1925 | Hopper | 362/103 |
| 3,638,011 | 1/1972 | Bain et al. | 362/103 |
| 3,811,684 | 5/1974 | Tredway, Sr. | 362/103 |
| 4,823,244 | 6/1989 | Alaybayoglu et al. | |
| 5,003,434 | 3/1991 | Gonser et al. | 362/32 |
| 5,086,378 | 2/1992 | Prince | 362/103 |
| 5,124,892 | 6/1992 | Lambert | 362/103 |

*Primary Examiner*—Albert J. Makay
*Assistant Examiner*—L. Heyman
*Attorney, Agent, or Firm*—Raymond Cranfill

[57] ABSTRACT

A surgical-type glove and illuminator assembly particularly adapted for use by health care professionals when examining or operating upon an anatomical part of a patient. A spotlighting illuminator is securely mounted on the fingers portion of the glove and oriented to project a light beam distally of the glove toward the work surface when the glove is in use. The illuminator may have a self-contained light source, or utilize fiber optic-transmitted light from a light source remote from the glove.

8 Claims, 2 Drawing Sheets

SURGICAL-TYPE GLOVE AND ILLUMINATOR ASSEMBLY

BACKGROUND OF THE INVENTION

This invention relates to protective gloves of the type worn by health care professionals when examining or operating upon patients, and more particularly, to an assembly of a surgical-type glove incorporating an illuminator for projecting light toward the work surface being examined or operated upon.

While the following discussion describes the present invention specifically in the context of its most prevalent use in the health care field, it will be understood that the invention is not intended to be so limited and has broader applicability to other fields where surgical-type gloves are normally employed. This would include, for example, its use by workers assembling small electronics parts where a contamination-free environment is essential.

When examining or operating upon an anatomical part of a patient, physicians, dentists and veterinarians will usually have available to them several different forms of lighting for illuminating their field of examination or operation. These include natural light entering the room through windows, overhead general room lighting, and directable high intensity lamps in fairly close proximity to the patient. Oftentimes, circumstances will require that these various sources of illumination be supplemented by a spotlighting type of illumination more examined or operated upon.

One approach for providing such spotlighting has been to incorporate illumination devices in combination with various medical and dental instruments. This type of approach is described, for example, in U.S. Pat. No. 4,823,244, issued Apr. 18, 1989, and U.S. Pat. No. 5,003,434, issued Mar. 26, 1991. In the devices described in these patents, light is transmitted through the bore of the instrument itself or its handle, and projected toward the body part under examination or operation through the distal tip of the instrument or distal ports in the handle. The light source may be, for example, a battery-powered lamp either housed entirely within the bore of the instrument or handle or detachably connected thereto. Alternatively, an optical fiber cable may be used for transmitting light to the bore of the instrument from a light source remote from the instrument.

The devices described in the above patents have certain inherent limitations. The relatively small size of the light output ports and their close proximity to the work surface, limit the work surface area that can be effectively illuminated by the projected light beam and permit little variance in the angle of projection of the light beam. Furthermore, since these devices rely upon the instrument or its handle being of hollow construction, this approach lacks universal applicability for use with all types of medical and dental instruments.

Regardless of the type and construction of the instrument being employed for performing any particular procedure, the professional's hand holding and manipulating the instrument will almost invariably be covered with a thin rubber or flexible plastic glove. Such surgical gloves are of standard construction well known in the art, and are universally worn over the hands of health care professionals when examining or operating upon body parts of patients.

SUMMARY OF THE INVENTION

It is, accordingly, a primary object of the present invention to provide a device for projecting a spotlighting type of illumination toward an anatomical part of a patient being examined or operated upon by a health care professional, having a wide range of applicability independent of the type and construction of the instrument being employed for the particular procedure.

Another object of the invention is to provide a device in accordance with the preceding object, which enables projection of a light beam at varying angles of projection easily controllable by the health care professional immediately as the need arises while performing the procedure.

A further object of the invention is to provide a device in accordance with the preceding objects, which enables projection of a light beam through a light output port sufficiently spaced from the work surface so as to effectively illuminate the required area of work surface.

The above and other objects are achieved in accordance with the present invention by incorporating a spotlighting illuminator in assembly with a surgical-type glove adapted to be worn over the hand of a health care professional when examining or operating upon an anatomical part of a patient. The illuminator is securely mounted on the fingers portion of the glove and oriented to project a light beam distally of the glove toward the anatomical part when the glove is in use. The illuminator includes a light housing terminating in a distally facing light output lens. The positioning of the illuminator on the glove is such as to enable sufficient spacing of the light output lens from the intended work surface for effective illumination of the required area of work surface, and to enable the angle of projection of the light beam to be easily controllable by simple finger movement of the wearer.

In one embodiment, the light source for the illuminator is a battery-powered lamp self-contained within the light housing. An alternative embodiment employs a light source remote from the glove, and includes at least one optical fiber extending lengthwise through the glove, with its distal end in communication with the interior of the light housing, and its proximal end adapted to be operably coupled to an optical fiber cable leading from the light source.

The invention, together with its embodiments, will be more fully described by the following detailed description considered in conjunction with the accompanying drawings.

DESCRIPTION OF PREFERRED EMBODIMENTS

Figure 1:
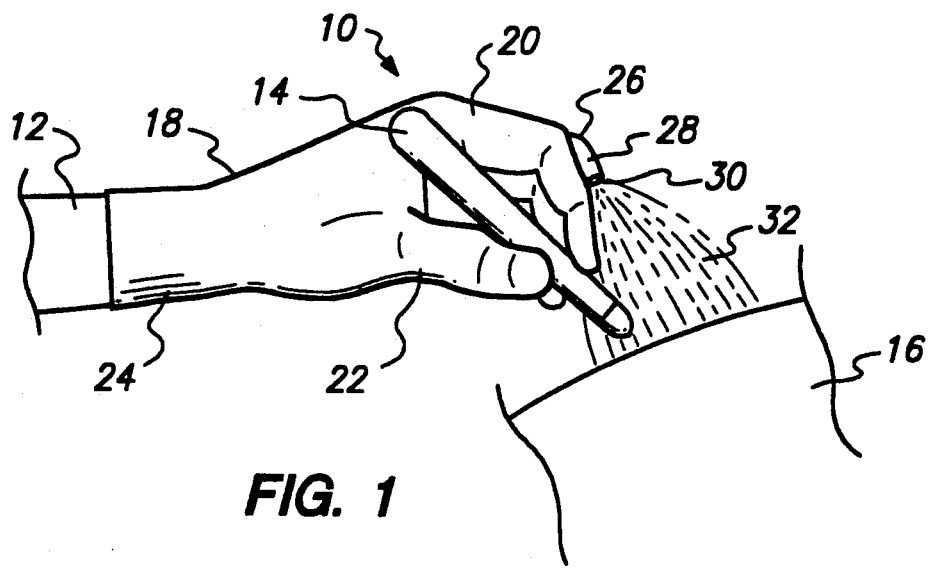
FIG. 1 is a side elevational view of a surgical-type glove and illuminator assembly in accordance with the present invention, being worn over the hand of a health care professional operating upon an anatomical part of a patient.

Referring now to the drawings, FIG. 1 illustrates a surgical-type glove and illuminator assembly 10 in accordance with the present invention. The assembly 10 is shown being worn over the hand of a surgeon 12 holding a surgical instrument 14 while operating upon an anatomical part of a patient 16.

The assembly 10 includes a surgical-type glove 18 of standard construction well known in the art, formed of thin rubber or flexible plastic, and having a distal fingers portion 20, an intermediate metacarpal portion 22, and a proximal wrist portion 24. An illuminator 26, having a light housing 28 terminating in a distally facing light output lens 30, is securely mounted on the topside of the fingers portion 20 of the glove 18, and oriented to project a light beam 32 distally of the glove 18 toward the anatomical part being operated upon.

The exact location at which the illuminator 26 is positioned on the glove 18, directly affects both the area of work surface that can be effectively illuminated by the light beam 32, and the ability of the wearer of the glove to control the angle of projection of such light beam. Positioning the illuminator 26 so as to overlie the middle phalanx of at least one of the fingers of the wearer enables the wearer to easily control the angle of projection of the light beam 32 by simple finger movement, and also provides the proper spacing of the lens 30 from the work surface for effective illumination of the required area of work surface. In the preferred embodiment illustrated in FIG. 1, the illuminator 26 is positioned so as to overlie the middle phalanx of the wearer's forefinger or index finger. As can be readily seen from FIG. 1, the work surface area effectively illuminated by the light beam 32 emanating from the device of the present invention, is much greater than would be possible by a light beam emanating from the distal tip of the instrument 14 similar to the prior art devices, due to the increased spacing of the lens 30 from the work surface.

Figure 2:
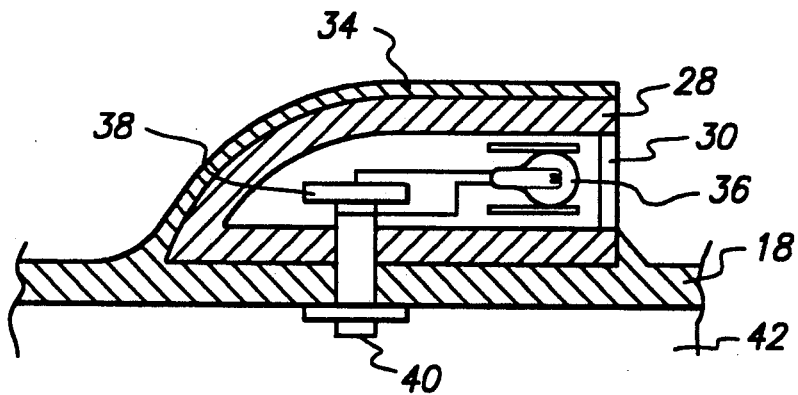
FIG. 2 is an enlarged fragmentary side elevational view of one embodiment of the assembly illustrated in FIG. 1, with portions broken away and sectioned to illustrate certain details of construction.
Figure 3:
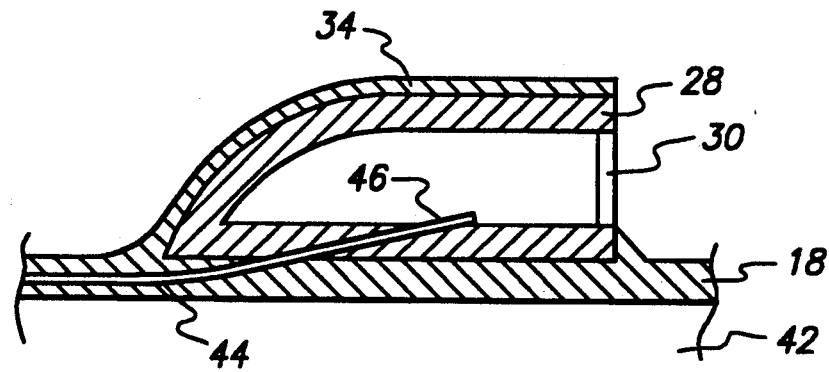
FIG. 3 is an enlarged fragmentary side elevational view similar to FIG. 2, but showing an alternative embodiment of the assembly illustrated in FIG. 1.

In order to ensure against accidental disengagement of the illuminator 26 from the glove 18, the illuminator must be mounted on the glove in a secure fashion. The preferred means for accomplishing this is illustrated in FIGS. 2 and 3. As shown, an encasement sheath 34 is formed integrally with the topside of the glove 18 and covers the housing 28 without obstructing the lens 30. This type of construction is particularly suitable for use with rubber gloves manufactured by dipping a mold into liquid latex, removing the mold from the liquid, and allowing the latex to dry. Insertion between successive latex dippings of the illuminator 26 with its lens 30 masked, and removal of the masking after final drying, will result in the integrally formed encasement sheath 34 shown in FIGS. 2 and 3. A similar effect can be achieved, but without the encasement sheath being formed integrally with the glove, by shrink-wrapping the illuminator 26 onto the topside of the glove 18 with thin plastic film which, if transparent, can also cover the lens 30.

FIG. 2 illustrates one embodiment of the assembly 10 shown in FIG. 1, wherein the light source for the illuminator 26 is self-contained within the light housing 28. In this embodiment, an incandescent bulb 36 and a battery 38 for powering the bulb, are both carried within the housing 28. The bulb 36 is operated by a push button switch 40 located on the underside of the housing 28 and which projects through the topside of the glove 18 into the interior 42 of the glove. In this manner, the switch is operable by finger movement of the wearer of the glove.

FIGS. 3 through 6 illustrate an alternative embodiment of the assembly 10 shown in FIG. 1, utilizing fiber optics to transmit light to the illuminator 26 from a light source remote from the glove. In this embodiment, at least one optical fiber 44 has a length thereof embedded within the material of the topside of the glove 18 and, as shown in FIG. 3, has its distal end 46 extending through the wall of the light housing 28 into communication with the interior of the housing and pointed toward the light output lens 30.

Figure 4:
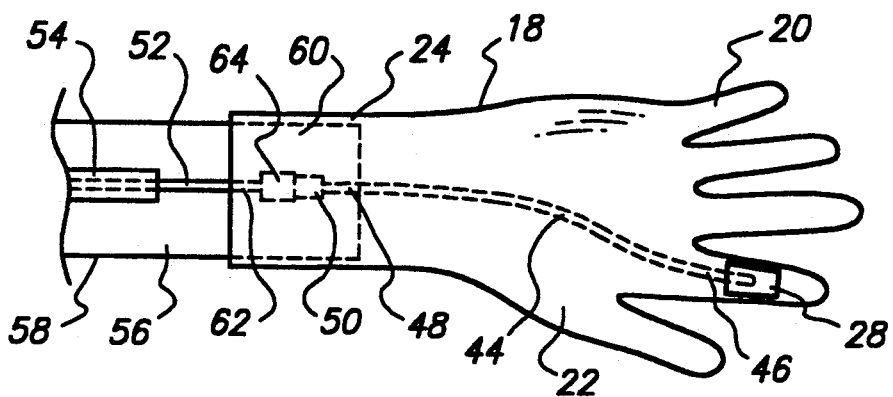
FIG. 4 is a top plan view of the assembly illustrated in FIG. 1 in flattened non-operating form, and further illustrating the alternative embodiment of FIG. 3.
Figure 5:
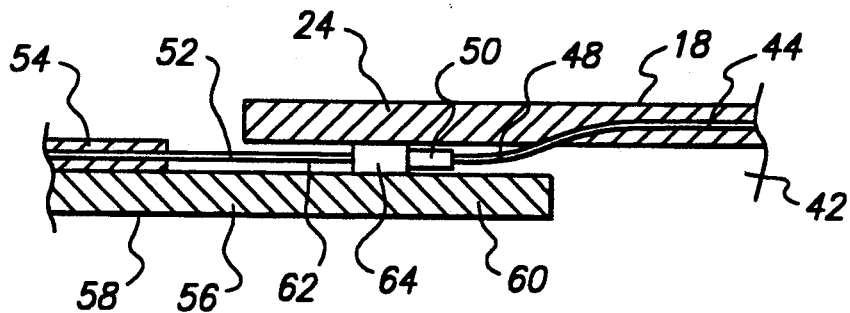
FIG. 5 is an enlarged fragmentary side elevational view of the assembly illustrated in FIG. 4, with portions broken away and sectioned to illustrate certain details of construction.

As shown in FIGS. 4 and 5, the length of optical fiber 44 embedded within the material of the topside of the glove 18, extends lengthwise from the housing 28 through the metacarpal portion 22 and into the wrist portion 24 of the glove 18. The proximal end 48 of the optical fiber 44 exits from the glove material into the interior 42 of the glove along the wrist portion 24, and terminates along the wrist portion 24 in a fiber optic coupler 50. Through the coupler 50, the optical fiber 44 is operably coupled to a fiber optic path leading from a remote light source (not shown), such as an electrically or battery powered lamp, enabling transmission of light from the light source to within the housing 28.

Particularly when the assembly of the present invention is being utilized in a surgical environment, a gown with wrist-length sleeves will normally be worn over the body of the user. Such surgical-type gowns are of standard construction well known in the art, and can be conveniently modified so as to be particularly suitable for use in conjunction with the fiber optics embodiment of the assembly of the present invention employing an optical fiber cable leading from the remote light source. The modification involves providing the gown with an attached casing through which the optical fiber cable can be suitably threaded. The casing extends along the sleeve of the gown from a point adjacent to the wrist end of the sleeve, up the sleeve, over the shoulder and down the back of the gown, and is secured to the gown along its entire length by suitable fastening means, such as stitching or adhesive. The use of such a casingmodified surgical-type gown in conjunction with the fiber optics embodiment of the assembly of the present invention, enables an optical fiber cable to be suitably threaded through the casing of the gown so that it exits from the casing at its proximal end along the back of the gown and at its distal end adjacent to its coupling location with the coupler 50 of the assembly of the present invention. This type of arrangement facilitates the coupling action while maintaining a sterile field, and also facilitates keeping the optical fiber cable out of the way of the surgeon during the surgical procedure.

Figure 6:
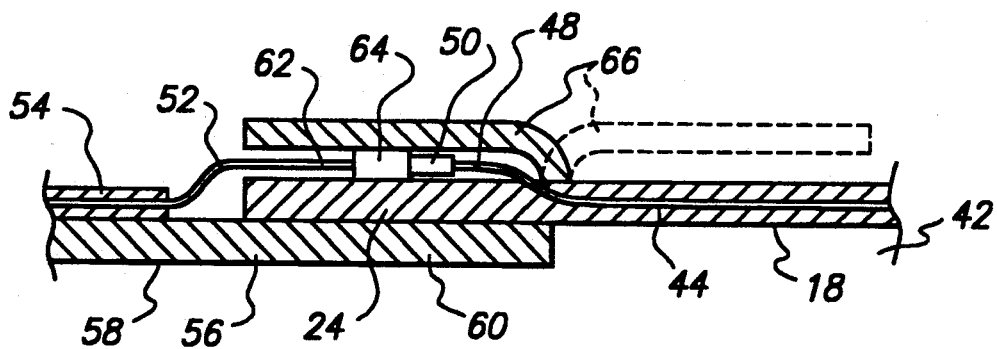
FIG. 6 is an enlarged fragmentary side elevational view similar to FIG. 5, but showing a modification of the embodiment illustrated in FIGS. 4 and 5.

The use of the casing-modified surgical-type gown described above in conjunction with the fiber optics embodiment of the assembly of the present invention, is illustrated in FIGS. 4 through 6. An optical fiber cable 52 leading from a remote light source (not shown) is threaded through and carried within a casing 54 secured along a sleeve 56 of a surgical-type gown 58 adapted to be worn over the body of the user, with the wrist end 60 of its sleeve 56 extending to the wrist of the user, and the wrist portion 24 of the glove 18 extending over the wrist end 60 of the sleeve 56. The distal end 62 of the optical fiber cable 52 exits from the casing 54 adjacent the wrist end 60 of the sleeve 56, and terminates in a coupler 64 adapted for coupling with the coupler 50 at a coupling location overlying the wrist end 60 of the sleeve 56. As shown in FIGS. 4 and 5, the coupling location directly overlies the wrist end 60 of the sleeve 56, and is covered by the wrist portion 24 of the glove 18. In this embodiment, the wrist portion 24 is rolled over on itself during the coupling action, and then rolled back after coupling has been effected FIG. 6 illustrates a modification of the embodiment shown in FIGS. 4 and 5. In the FIG. 6 modification, the proximal end 48 of the optical fiber 44 exits from the glove material along the wrist portion 24, but exteriorly f the glove body, so that the coupling location between the couplers 50 and 64 overlies the wrist portion 24 of the glove 18 as well as the wrist end 60 of the sleeve 56. With this modification, the assembly is further provided with a cuff 66 attached to the exterior of the glove 18 so as to be pivotable between a distally extending position (shown in broken lines) exposing the coupling location, and a proximally extending position (shown in solid lines) covering the coupling location. The cuff is in the distally extending position during the coupling action, and then pivoted to the proximally extending position after coupling has been effected.

Having thus described the invention, what is desired to be protected by Letters Patent is presented by the following appended claims.

What is claimed is:

1. A surgical-type glove and illuminator assembly, said assembly comprising:
 a) a surgical-type glove having a distal fingers portion, said glove adapted to be worn over a hand of a user when examining or operating on a work surface; and
 b) illumination means for providing light to the work surface, said illumination means comprising:
  i) a light housing mounted on an exterior surface of said fingers portion of the surgical-type glove and terminating in a distally facing light output lens, the light housing further characterized in having an underside substantially adjacent to the surgical-type glove and a topside substantially opposite the underside,
  ii) a self-containing battery-powered light source carried within the light housing, and
  iii) switch means for operating the light source, the switch means located on the underside of the light housing and extending through and interior of said fingers portion of the surgical-type glove so as to be operable by finger movement of the user.

2. A surgical-type glove formed from a material and illuminator assembly, said assembly comprising:
 a) a surgical-type glove having a distal fingers portion, an intermediate metacarpal portion and a proximal wrist portion, said glove adapted to be worn over a hand of a user when examining or operating on a work surface; and
 b) illumination means for providing light to the work surface, said illumination means comprising:
  i) a light housing mounted on an exterior surface of said fingers portion of the surgical-type glove and terminating in a distally facing light output lens, and
  ii) at lest one optical fiber having a distal end in communication with the light output lens of the light housing and a proximal end terminating in a coupling means at a desired coupling location for operably coupling said at least one optical fiber to a fiber optic path leading from a light source remote from the glove said at least one optical fiber being embedded within said material
 wherein said at lest one optical fiber receives light from the remote light source via the coupling means and carries the light to the light output lens of the light housing.

3. The assembly of claim 2 wherein the proximal end of said at least one optical fiber exits from the glove interiorly and said coupling location is covered by the proximal wrist portion of the glove.

4. The assembly of claim 3 wherein said fiber optic path comprises an optical fiber cable carried within a casing secured along a sleeve of a surgical-type gown adapted to be worn by the user and the proximal wrist portion of the glove extends over the sleeve at the coupling location, the optical fiber cable exiting from the casing adjacent to the coupling location.

5. The assembly of claim 4 wherein the casing extends over the shoulder and down the back of the surgical-type gown and is secured to said gown along its entire length, and the optical fiber cable exits from said casing along the back of the gown.

6. The assembly of claim 2 wherein the proximal end of said at least one optical fiber exits exteriorly of the glove, and said assembly further comprises a cuff means attached exteriorly of said glove so as to be pivotable between a distally extending position exposing the coupling location and a proximally extending position covering the coupling location.

7. The assembly of claim 6 wherein the fiber optic path comprises an optical fiber cable carried within a casing secured along a sleeve of a surgical-type gown adapted to be worn over the body of said user in conjunction with said assembly so that the sleeve extends to the wrist of the user and the proximal wrist portion of the glove extends over the sleeve at the coupling location, the optical fiber cable exiting from said casing adjacent to the coupling location.

8. The assembly of claim 7, wherein the casing extends over the shoulder and down the back of the gown and is secured to the gown along its entire length, and the optical fiber cable exits from the casing along the back of the gown.

* * * * *